United States Patent [19]

Bianco

[11] 4,092,315
[45] May 30, 1978

[54] NOVEL CRYSTALLINE FORMS OF PRAZOSIN HYDROCHLORIDE

[75] Inventor: Ernest J. Bianco, Niantic, Conn.

[73] Assignee: Pfizer Inc., New York, N.Y.

[21] Appl. No.: 662,937

[22] Filed: Mar. 1, 1976

[51] Int. Cl.² ............................................. C07D 239/94
[52] U.S. Cl. ..................................... 544/291; 424/251
[58] Field of Search .................. 260/256.4 Q; 424/251

[56] References Cited
U.S. PATENT DOCUMENTS

| 3,635,979 | 1/1972 | Hess | 260/256.4 Q |
| 3,663,706 | 5/1972 | Hess | 424/251 |

OTHER PUBLICATIONS

Weissberger, A. Ed., "Technique of Organic Chem.", vol. III, Interscience N.Y., N.Y., (1950).

Primary Examiner—Alton D. Rollins
Assistant Examiner—D. B. Springer
Attorney, Agent, or Firm—Connolly and Hutz

[57] ABSTRACT

The invention relates to novel and valuable crystalline forms of the hypotensive agent prazosin hydrochloride. The anhydrous α-form is preferred because it is relatively non-hygroscopic and hence possesses important advantages in handling and formulation. The polyhydrate form of prazosin hydrochloride is preferred because of its low, uniform rate of dissolution.

4 Claims, 6 Drawing Figures

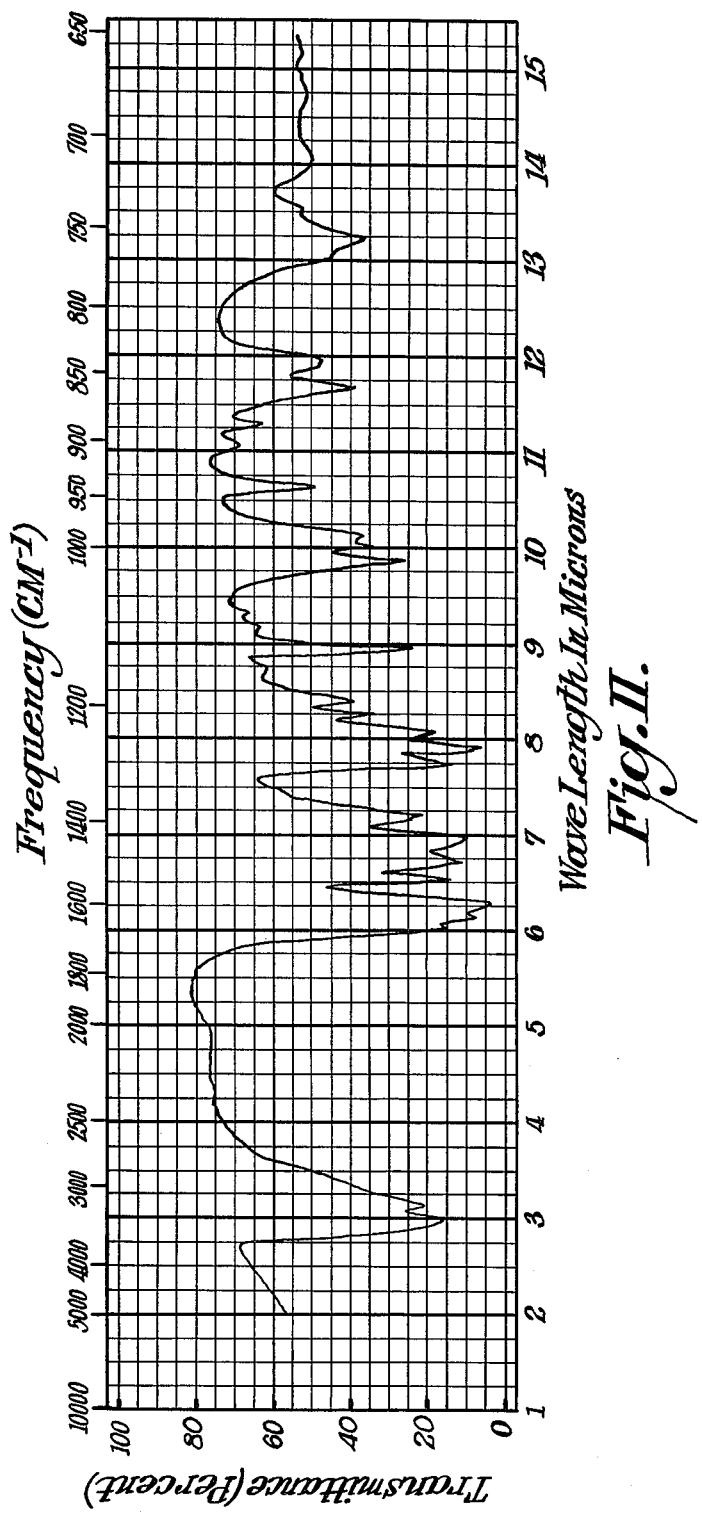
Fig. II.

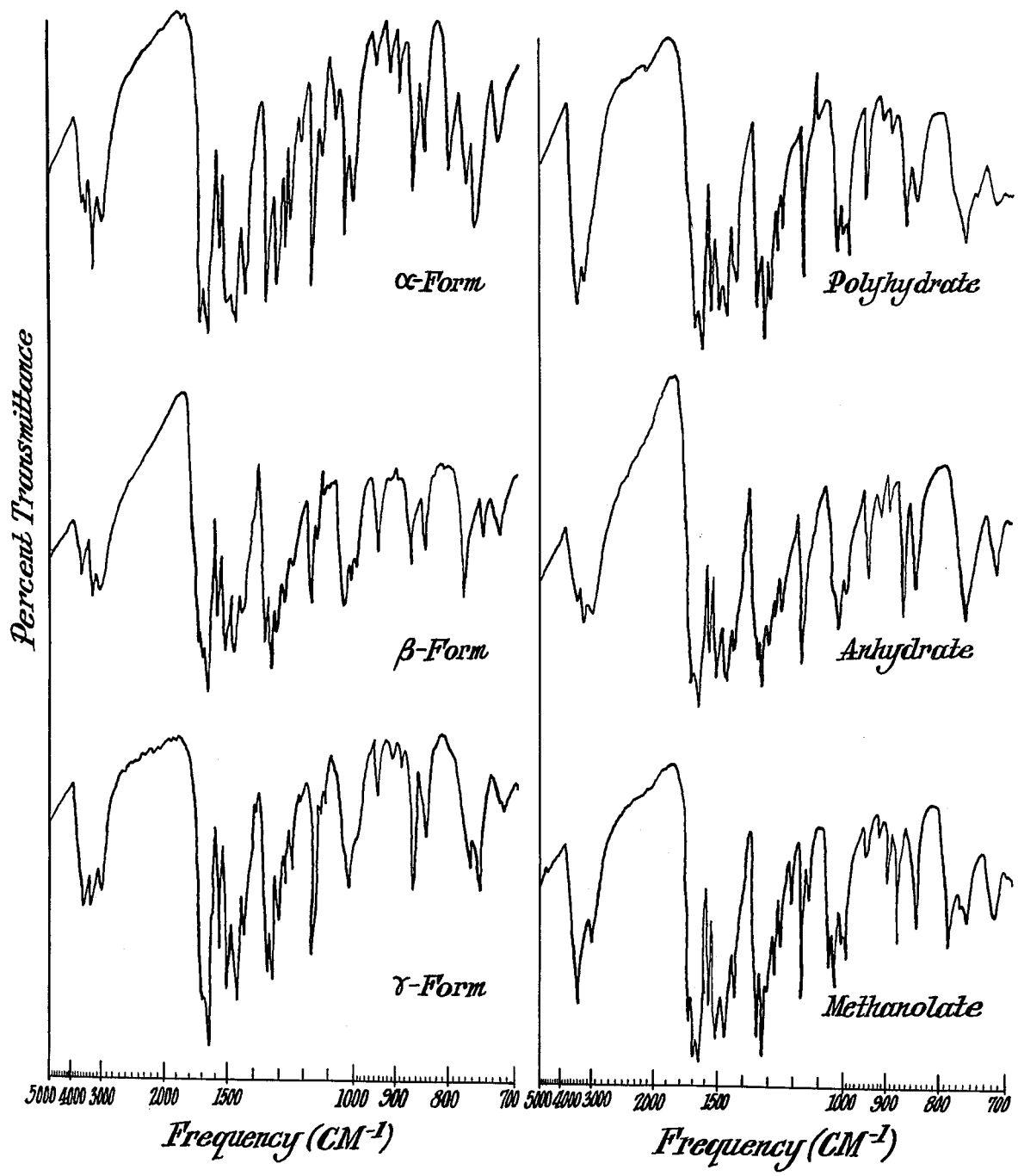
Fig. III.

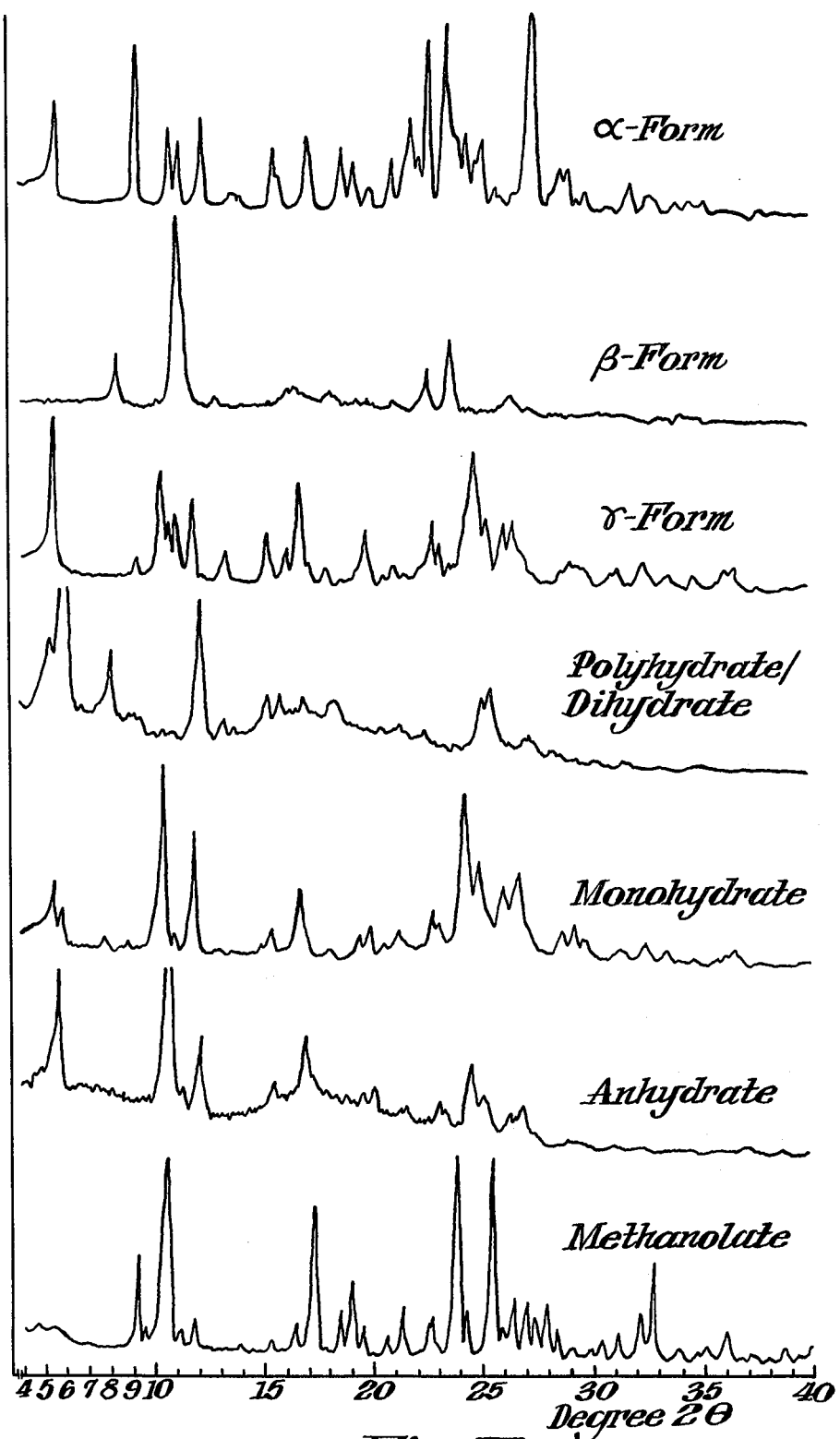
Fig. IV.

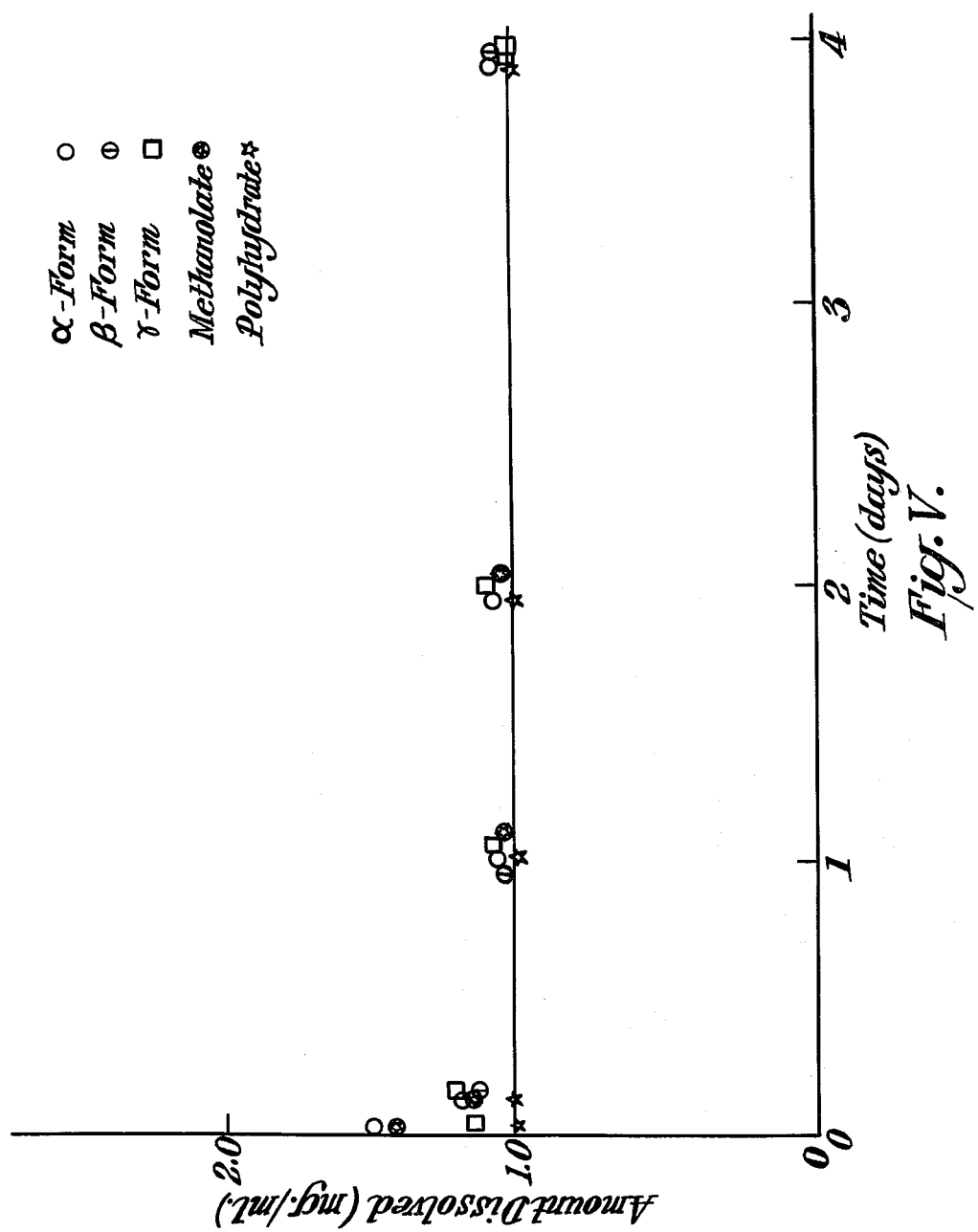
Fig. V.

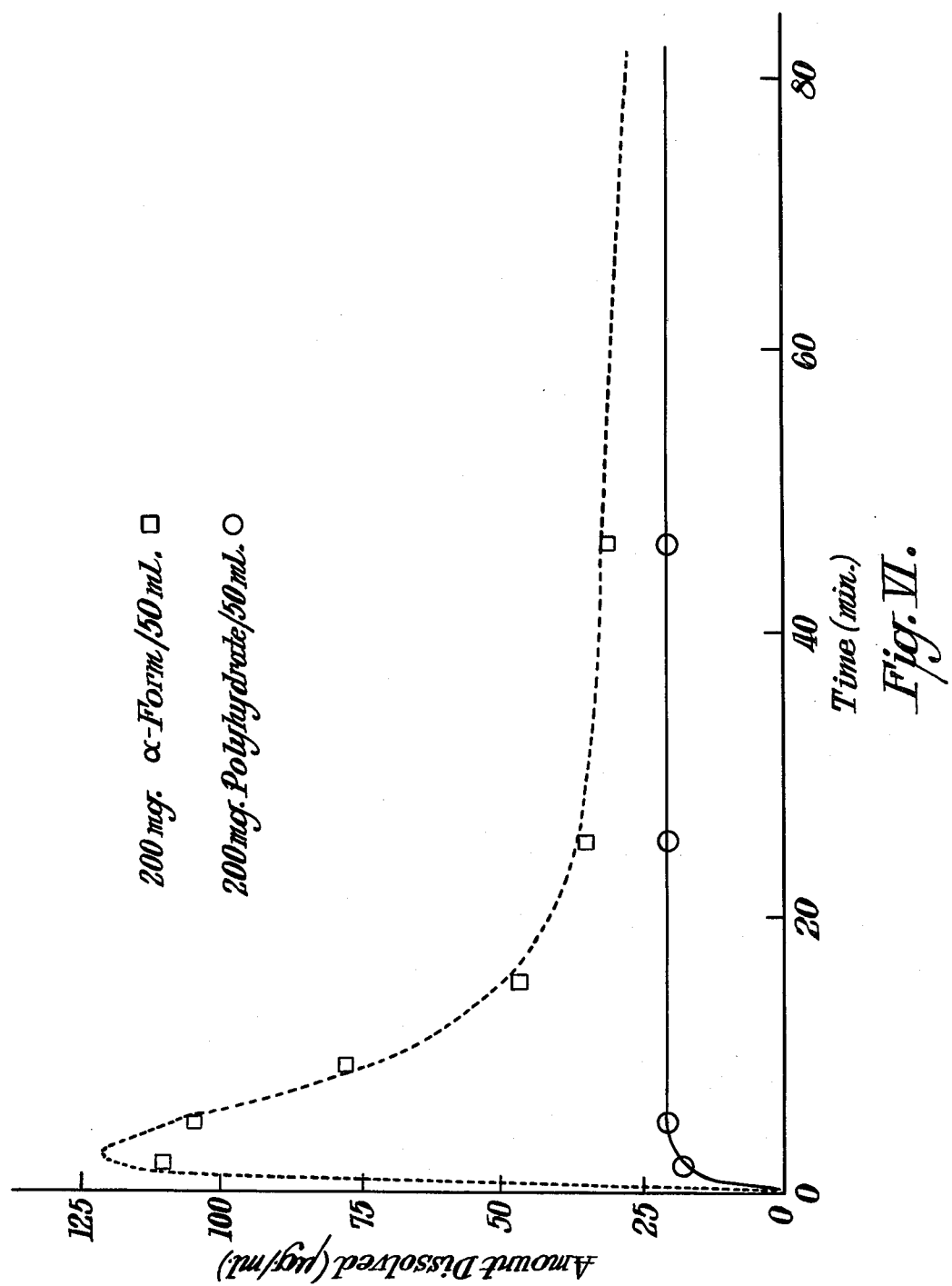
Fig. VI.

NOVEL CRYSTALLINE FORMS OF PRAZOSIN HYDROCHLORIDE

BACKGROUND OF THE INVENTION

1. Field of the Invention

The invention pertains to the novel, relatively non-hygroscopic, crystalline α-form of the valuable hypotensive agent prazosin hydrochloride of the formula:

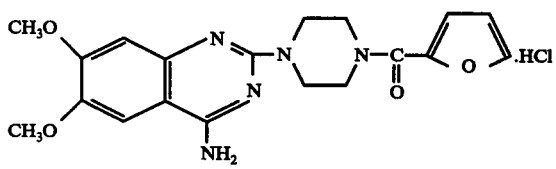

and processes for preparing said crystalline α-form, as well as the novel, crystalline polyhydrate form of prazosin hydrochloride which has a low, uniform rate of dissolution.

2. Description of the Prior Art

U.S. Pat. Nos. 3,511,836, 3,635,979 and 3,663,706 disclose 2-[4-(2-furoyl)piperazin-1-yl]-4-amino-6,7-dimethoxyquinazoline. The first of these U.S. Patents specifically claims this compound and its acid addition salts and U.S. Pat. No. 3,663,706 claims the use of the compound and its pharmaceutically acceptable acid addition salts as valuable hypotensive agents. Pharmacological studies on 2-[4-(2-furoyl)piperazin-1-yl]-4-amino-6,7-dimethoxyquinazoline hydrochloride, hereinafter designated by its generic name, prazosin hydrochloride, were reported by Scriabine et al., *Experientia*, 24, 1150(1968), and by Constantine et al., in "Hypertension: Mechanisms and Management", Onesti et al., editors, Grune and Stratton, Inc., 1973, p. 429–444. Preliminary clinical studies on prazosin hydrochloride were reported by Cohen, *J. Clin. Pharmacol.*, 10, 408(1970). Side effects due to initial doses of prazosin have been reported by Bendall et al., Brit. Med. Jour., 2, 727(1975).

DESCRIPTION OF THE DRAWINGS

FIG. I is the infrared spectrum of the α-form of prazosin hydrochloride in KBr.

FIG. II is the infrared spectrum of prazosin hydrochloride polyhydrate in KBr.

Figure 1:
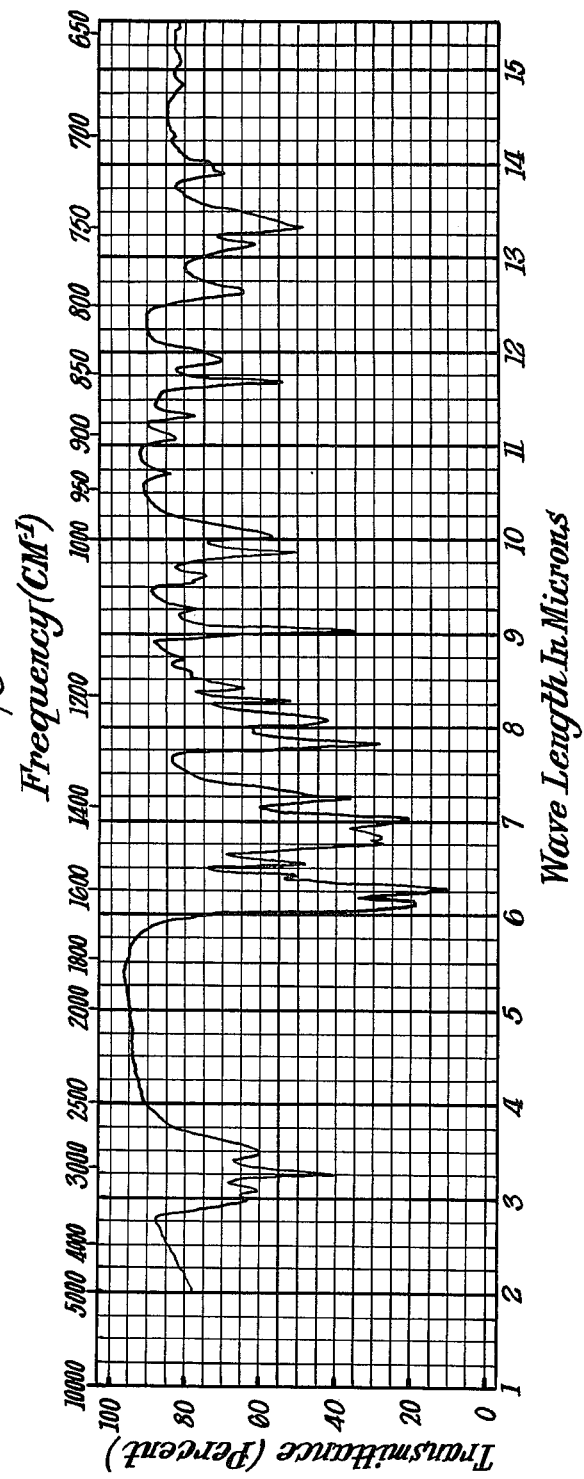

FIG. III is representative infrared spectra of various crystalline modifications of prazosin hydrochloride.

FIG. IV is representative X-ray diffractograms of various crystalline modifications of prazosin hydrochloride.

FIG. V is the powder dissolution profile of various crystalline modifications of prazosin hydrochloride in water at 25° C.

FIG. VI is the powder dissolution profiles of prazosin hydrochloride, α-form and polyhydrate in simulated gastric juice at 25° C.

SUMMARY

It is an object of this invention to provide a novel crystalline polymorph of 2-[4-(2-furoyl)piperazin-1-yl]-4-amino-6,7-dimethoxyquinazoline hydrochloride herein designated as the α-form of prazosin hydrochloride, characterized by the infrared spectrum in potassium bromide having the following absorption bands:

| Wavelength, Microns | Wavelength, Microns | Wavelength, Microns |
| --- | --- | --- |
| 2.95 | 7.30 | 10.67 |
| 3.10 | 7.81 | 11.05 |
| 3.25 | 8.08 | 11.30 |
| 3.50 | 8.28 | 11.66 |
| 6.12 | 8.40 | 11.90 |
| 6.26 | 8.70 | 12.60 |
| 6.39 | 9.02 | 13.10 |
| 6.54 | 9.25 | 13.31 |
| 6.75 | 9.60 | 13.87 |
| 6.81 | 9.85 | 13.95 |
| 7.02 | 10.02 | 14.82 |
| 7.22 | | |

Another object of this invention is to provide a new crystalline anhydrous form of prazosin hydrochloride which is relatively non-hygroscopic and stable.

Yet another object of the invention is to provide the novel crystalline hydrates of 2-[4-(furoyl)piperazin-1-yl]-4-amino-6,7-dimethoxyquinazoline hyrochloride characterized by the infrared spectrum in potassium bromide having the following absorption bands:

| Wavelength, Microns | Wavelength, Microns | Wavelength, Microns |
| --- | --- | --- |
| 2.98 | 7.80 | 10.15 |
| 3.14 | 7.95 | 10.66 |
| 6.04 | 8.08 | 11.10 |
| 6.14 | 8.27 | 11.31 |
| 6.30 | 8.40 | 11.70 |
| 6.53 | 8.75 | 11.90 |
| 6.72 | 8.96 | 12.00 |
| 6.95 | 9.17 | 13.10 |
| 7.15 | 9.33 | 13.27 |
| 7.21 | 9.85 | 13.57 |
| 7.73 | 10.03 | 14.05 | and further characterized by containing from about 8 to 15% by weight of water.

Still another object of the invention is to provide a process for producing a hypotensive effect which comprises administering to a hypertensive host a hypotensive effective amount of said hydrate of prazosin hydrochloride.

DETAILED DESCRIPTION OF THE INVENTION

The present invention is based on the discovery of two novel, crystalline forms of the valuable hypotensive agent prazosin hydrochloride which have decided advantages over other forms of this drug. The first of these novel crystalline forms of prazosin hydrochloride is an anhydrous form herein designated as the "α-form". The α-form has been found to be relatively non-hygroscopic and stable. It thus possesses important advantages in handling, storing and formulation. Other crystalline, anhydrous, unsolvated forms of prazosin hydrochloride disclosed herein are designated, for convenience, the "β-form", the "γ-form" and "anhydrate". Also disclosed is the solvate, prazosin hydrochloride methanolate.

As used herein the term "relatively non-hygroscopic" means that a sample, initially containing not more than about 0.5% water, when exposed to a temperature of about 37° C. and a relative humidity of about 75% for a period of about 30 days, contains not materially in excess of 1.5% water. Prazosin hydrochloride having up to but not materially in excess of about 1.5% water is considered to be anhydrous within the context of this invention.

The second novel crystalline form of prazosin hydrochloride which has decided advantage over other forms of this drug is herein designated as the "polyhydrate". It has now been found that when any of the other forms of prazosin hydrochloride are crystallized from an aqueous medium or mixtures of water and organic solvents, followed by drying until the water content of the resulting crystals is in the range of about 8 to 15% by weight as determined by the well-known Karl Fischer method for determination of water, prazosin hydrochloride polyhydrate is obtained. At the lower end of this range of water content, that is at about 8% water by weight, the stiochiometry corresponds to a dihydrate of prazosin hydrochloride having about two moles of water per mole of prazosin hydrochloride. Said dihydrate is within the scope and purview of this invention. Especially preferred, however, is prazosin hydrochloride polyhydrate having from about 12 to 15% water by weight because it is more readily obtained and has less tendency to absorb water than other hydrates of prazosin hydrochloride.

The polyhydrate may be prepared, for example, by crystallization of prazosin hydrochloride from hot water or from mixtures of water and organic solvents followed by filtering and drying the crystals until the moisture content is in the desired range of about 8 to 15% by weight. When mixtures of water and organic solvents are employed, suitable organic solvents are water miscible organic solvents such as methanol, ethanol, isopropanol, acetone, methyl ethyl ketone, and the like as well as mixtures of such water miscible organic solvents with water immiscible organic solvents such as dichloromethane, chloroform, hexane, benzene, toluene and the like. An alternate method for preparing prazosin hydrochloride polyhydrate is by trituration of anhydrous prazosin hydrochloride with water followed by drying the resulting crystals to the desired moisture content.

As mentioned above, the water content of the polyhydrate can vary from about 8 to about 15% or more. From X-ray diffraction data, presented below, it appears that only up to two molecules of water per molecule of prazosin hydrochloride are bound in the crystal lattice. The remaining water is free interstitial water.

When a sample of prazosin hyrochloride polyhydrate containing from about 12 to 15% water by weight is further exposed to drying conditions, such as storage in a desiccator or heating in a vacuum oven, moisture loss occurs until the dihydrate containing about 8.0% moisture is obtained. Heating at 100° C. in a vacuum oven or vacuum desiccator will ordinarily suffice. Further heating will, in turn, provide the monohydrate containing about 4.1% moisture. Still further heating leads to the formation of prazosin hydrochloride anhydrate.

The preferred, novel and valuable α-form of prazosin hydrochloride is readily and reproducibly obtained by heating any of the forms of prazosin hydrochloride, including the hydrates and solvate in the presence of a suitable organic solvent at a temperature in the range of about 100° to 200° C. and preferably in the presence of an alcoholic solvent at a temperature in the range of about 125°–160° C. Preferred alcoholic solvents are the aliphatic and alicyclic alcohols having from about 5 to 7 carbon atoms. Examples of such alcohols are isoamyl alcohol, n-pentanol, 2-methyl-1-butanol, cyclopentanol, 1-methylcyclopentanol, 2-methylcyclopentanol, cyclohexanol, 1-methylcyclohexanol, 3-methylcyclohexanol, 2-methyl-3-pentanol, 4-methyl-1-pentanol, 2-methyl-3-hexanol, 2-methyl-2-hexanol, cycloheptanol and the like. Especially preferred for producing the α-form of prazosin hydrochloride is isoamyl alcohol, also known as 3-methyl-1-butanol, because of its ready availability and efficiency in forming the desired crystalline polymorph of prazosin hydrochloride. For convenience, the preferred temperature for formation of the α-form when isoamyl alcohol is employed is about 132° C. which is the boiling point of this alcohol at atmospheric pressure.

In carrying out the process to prepare the α-form of prazosin hydrochloride it is preferred to use an amount of alcoholic solvent sufficient to effect at least a partial solution of prazosin hydrochloride when the mixture is heated to a temperature within the preferred range of temperature. Ordinarily, from about 4 to 25 ml. of such alcohol per gram of prazosin hydrochloride will suffice, although, more or less than this amount of alcohol may be employed in some instances with satisfactory results.

The heating time required to effect substantially complete formation of the α-form of prazosin hydrochloride by the above process can vary from as little as a few minutes to about 6 hours or more. The optimal time required in a given instance will vary with several factors such as the precise temperature and the particular alcohol used as solvent. When the process is carried out in refluxing isoamyl alcohol the time required to effect substantially complete formation of the desired α-form is ordinarily about 2–3 hours. The extent of formation of the α-form of prazosin hydrochloride may be conveniently monitored by removal of a sample, cooling to room temperature, isolating the precipitate by filtration and obtaining an infrared spectrum in potassium bromide of the precipitate. As shown below, each of the non-hydrated forms of prazosin hydrochloride has a characteristic infrared spectrum.

When the starting prazosin hydrochloride employed is a solvate such as the methanolate or one of the hydrates, it is preferable, although not essential, to remove the molecules of solvation or hydration by distilling off, e.g., methanol or water during the heating period required to obtain the α-form of prazosin hydrochloride by the above process.

If, in carrying out the above process, the prazosin hydrochloride is heated in an alcoholic solvent such as isoamyl alcohol but at a temperature somewhat below about 125° C., or even when heated at a higher temperature, within the above-mentioned preferred range of temperature for preparing the α-form of prazosin hydrochloride, but for an insufficient length of time, the resulting product will be either the crystalline polymorph of prazosin hydrochloride herein designated as the γ-form, or a mixture of α-form and γ-form.

The methanolate of prazosin hydrochloride may be obtained by slurrying any of the essentially anhydrous forms of prazosin hydrochloride in methanol. At room temperature, ordinarily, about 3 hours is sufficient. The methanolate may be formed more rapidly by heating at a higher temperature. For example, at the boiling point of methanol, solvate formation is complete in about 10 minutes. The product is isolated by standard methods. Elemental analysis of the methanolate reveals that the prazosin hydrochloride and methanol are combined in a 1:1 mole ratio.

The β-form of prazosin hydrochloride is obtained when the above methanolate is exposed to temperatures sufficient to remove the solvate molecule. For example, heating the methanolate at 135° C. for about 12 hours or 110° C. for about 24 hours. Removal of methanol is facilitated by carrying out the above thermal exposure at reduced pressure, e.g., in a vacuum oven.

CHARACTERIZATION OF THE VARIOUS FORMS OF PRAZOSIN HYDROCHLORIDE

Infrared Spectra

The infrared spectra of the three anhydrous crystalline forms of prazosin hydrochloride, the methanolate, the hydrates and the amorphous dehydrate when obtained by standard methods either as a KBr pellet or Mujol mull, provide a rapid and convenient method for characterizing these forms. However, infrared spectroscopy did not discriminate the various hydrated forms from one another. The characteristic infrared spectrum of the α-form of prazosin hydrochloride is shown in FIG. I. The infrared spectrum of FIG. II was obtained with a sample of prazosin hydrochloride polyhydrate (12% moisture). The infrared spectrum together with the water content of the sample can be used to characterize the polyhydrate. The infrared spectra (KBr) of the α-, β- and γ-polymorphs, the polyhydrate, the anhydrate and the methanolate of prazosin hydrochloride are compared in FIG. III. The spectra are representative of those obtained on a Perkin-Elmer Model 21 recording infrared spectrophotometer employing potassium bromide pellets prepared by intimately grinding in a mortar and pestle 1 mg. of the appropriate sample with 300 mg. of KBr. The mixture is then placed in a Perkin Elmer die press model No. 1860025 and the die subjected to 15,000 p.s.i., under vacuum for one minute.

Characteristic infrared absorption bands which may be used for differentiating the various forms of prazosin hydrochloride from one another are listed in Table I.

TABLE I

| Form of Prazosin . HCl | Characteristic Bands | | |
|---|---|---|---|
| | cm$^{-1}$ | μ | comment |
| α— | 795 | 12.6 | sharp |
| β— | 770 | 13 | sharp |
| γ— | 770, 743 | 13, 13.4 | doublet |
| Hydrates* | 1260 | 7.95 | sharp |
| | 755 | 13.3 | broad |
| | 1000 | 10 | doublet |
| Anhydrate | 1260 | 7.95 | sharp |
| | 755 | 13.3 | |
| | 1005 | 9.95 | triplet |

*The infrared spectra of the monohydrate (4.1% H$_2$O), dihydrate (7.9% H$_2$O) and polyhydrate were identical.

When samples of the α-, β- and γ- polymorphs are triturated with water the resulting product in each case is found to give an infrared spectrum identical to that of the prazosin hydrochloride hydrates.

X-ray Diffractometry

X-ray powder diffraction patterns were obtained on a Siemens diffractomer equipped with nickel-filtered copper radiation and a scintillation counter detector. Beam intensity as a function of the angle 2θ was recorded at a scanning rate of 1° per minute.

Characteristic diffractograms of each of the modifications of prazosin hydrochloride examined are shown in FIG. IV. The peaks (expressed in "degrees 2θ") which may be used to distinguish one form from another are summarized below in Table II.

TABLE II

| Form of Prazosin . HCl | Characteristic Peaks, degrees 2θ |
|---|---|
| α— | 1:3:3:1 quartet centered at 23°; sharp bands at 9.3° and 27.5°. |
| β— | sharp bands at 11.3°, 22.5°, 23.6° |
| γ— | band groupings at 10.5°, 16.7° 24.8° |
| Polyhydrate/dihydrate* | sharp bands at 8.05°, 12.2°; doublet at 25.2° |
| Monohydrate | sharp bands at 10.5, 12.0°, 16.9° doublets at 24.5°, 26.5° |
| Anhydrate | not significantly different than the monohydrate |
| Methanolate | sharp bands at 10.5°, 17.3°, 23.9°, 25.5° |

*The diffractogram for the polyhydrate containing about 15% water is not significantly different than that obtained for the dihydrate. This indicates that only two molecules of water per molecule of prazosin hydrochloride are actually bound in the crystal lattice, the remaining water in the polyhydrate is free interstitial water.

The X-ray diffractograms further confirmed the differences between the α-, β-, γ- and anhydrate forms of prazosin hydrochloride. The combination of X-ray analysis and moisture determination also provides a method for characterizing the various hydrates.

Differential Scanning Calorimetry (DSC)

Samples (1–2 mg.) were analyzed on a Mettler DTA 2000 thermal analyzer at a range of 50 microvolts or 100 microvolts and at a heating rate of 5° per minute. Results obtained are summarized in Tables III and IV.

TABLE III

Summary of DSC Data on Samples of Various Forms of Prazosin Hydrochloride (Heating rate, 5° per minute; Samples introduced at about 40°; Temperatures in ° C.)

| | |
|---|---|
| α-Form | Single endotherm at 279° |
| γ-Form | Partially resolved endothermic doublet at 270° (medium) and 278° (strong) |
| Polyhydrate | Broad endotherm from about 60° to 160° with peak at 110°, weak endotherm at 183°, medium exotherm at 195°, strong endotherm at 265°. |
| Methanolate | Broad endotherm at 137°, sharp medium endotherm at 167° and sharp strong endotherm at 278° C. |

TABLE IV

Summary of DSC Data on Samples of Crystalline Polymorphs of Prazosin Hydrochloride (Heating rate, 5° per minute; Samples introduced at about 250°; Temperatures in ° C.)

| | |
|---|---|
| α-Form | Unresolved endothermic doublet at 263° |
| β-Form | Partially resolved endothermic doublet at 263° (strong) and 263.5° (medium) |
| γ-Form | Partially resolved endothermic doublet at 261.5° (strong) and 262.5° (medium) |

Interpretation of the differential scanning calorimetry data is complicated by decomposition that occurs during fusion. No sign of polymorphic conversion was observed by DSC, which indicates that the polymorphic forms are solvent-induced and that their conversion points are beyond their decomposition temperatures. Although each of the forms of prazosin hydrochloride appeared to have unique DSC behavior, the characteristics of each are heavily dependent upon testing conditions. Adjustments in instrumental parameters were found capable of inducing different DSC patterns for a given polymorph or solvate. The doublet pattern of the γ-Form of prazosin hydrochloride, for example, was found to vary as a function of heating rate, starting temperature and sample size.

Methanol could only be removed from the methanolate between about 130° and 140° C. well above its boiling point of 65° C. This suggests that strong bonding forces exist in this solvate between methanol and prazosin hydrochloride. By contrast, the polyhydrate loses water rapidly at temperatures approaching the boiling point of free water, indicating that at least some of the water present was unbound and occupied only an interstitial position within the dihydrate lattice.

Hygroscopicity

Since moisture uptake affects integrity of a drug form, the α-, β- and γ- crystalline polymorphs of prazosin hydrochloride were compared for their relative hygroscopicity. Samples of each polymorph were placed in an open beaker and stored in a chamber maintained at 37° C. and 75% relative humidity. Portions were withdrawn periodically and their water content determined by the Karl Fischer method. Results are listed in Table V.

TABLE V

Water Content of Samples Exposed to 37° C., 75% R.H.

| Exposure Time, Days | Water Content, % by Weight Prazosin Hydrochloride | | |
|---|---|---|---|
| | α-Form | β-Form | γ-Form |
| 5 | 0.32 | 0.59 | 0.16 |
| 12 | 0.85 | 1.18 | 4.61 |
| 25 | 1.18 | 4.66 | 9.47 |
| 34 | 1.54 | 6.06 | 9.05 |

As the above data indicates, the α-form of prazosin hydrochloride is relatively non-hydroscopic when compared with the β- and γ-forms. Changes in the infrared spectrum (KBr pellet) of a sample of the γ-form of prazosin hydrochloride after such exposure to moisture confirmed the formation of a hydrate.

Samples of prazosin hydrochloride polyhydrate, initially containing 13.7% water were exposed at 37° C. and 75% relative humidity. After 10 and 23 days the water content was 13.2 and 13.4%, respectively. A sample, initially containing 13.5% water upon exposure at room temperature and 20% relative humidity was found to contain 13.0% water after 18 days and 13.1% water after 35 days.

Microscopy

Upon examination with a light microscope at 200X magnification, the α-form and the methanolate of prazosin hydrochloride are found to be comprised of rod-like crystals, with those of the methanolate being much larger in size. The β-form consisted of dark, monoclinic crystals, while the γ-form and polyhydrate are both needle-like crystals.

When a drop of water is added to each of the three microscope slides containing α-, β-, and γ-forms of prazosin hydrochloride, sharp needle-like crystals of hydrate grew and joined together to form a spectacular, hair-like nematic array, characteristic of a liquid crystalline phase. This is in agreement with the above mentioned change in the infrared spectra of the α-, β-, γ-polymorphs to that of the hydrates of prazosin hydrochloride upon trituration of each of the crystalline polymorphs with water. Stability Studies Stability studies were carried out on bulk lots of the α-form, β-form, γ-form and the polyhydrate of prazosin hydrochloride. Samples were stored in an oven maintained at 50° C., and others were stored at 25° C. while exposing them to sunlight.

All samples were stored in clear glass bottles. After such storage for 6 weeks and again at 12 weeks the samples were observed for any visual or chemical changes. All samples were found to have good chemical stability. However, the sample of polyhydrate that was exposed to sunlight exhibited some photodegradation as evidenced by visible color change from white to yellow-pink at 6 weeks and to orange at 12 weeks. The other forms of prazosin hydrochloride were stable to sunlight throughout the test period.

When samples of prazosin hydrochloride polyhydrate are stored in ambler glass bottles at 25° C. while exposing them to sunlight, no changes are evident after 12 weeks.

Dissolution Studies

To measure the rate of dissolution of the powdered drug in water, 100 mg. of fine powder was added to 50 ml. of water contained in a 100 ml. volumetric flask. The stoppered flask was shaken in a wrist-action shaker in a 25° C. water bath. Samples were withdrawn periodically, filtered through a Millipore filter (0.45mμ pore size), then analyzed spectrophotometrically on a Beckman Acta III spectrophotometer. The slopes of Beer's law plots for prazosin hydrochloride at 246 nm. and 330 nm. were used to calculate solubility of the powders. FIG. V depicts the powder dissolution profiles in water of the α-form, β-form, γ-form, the methanolate and polyhydrate of prazosin hydrochloride. While the data for polyhydrate is uniform throughout the 4 days of the experiment, the other forms of prazosin hydrochloride each show greater initial solubility with gradual decline in solubility to that of the polyhydrate.

FIG. VI summarizes the results of the powder dissolution data obtained in the same manner as described above, except that 200 mg. of solute in 50 ml. of USP simulated gastric juice (SGJ) was used in each case. The α-form of prazosin hydrochloride attained maximum solubility in about 5 minutes and solubility declined gradually throughout the experiment, finally approaching that of the polyhydrate. The polyhydrate also reached its maximum solubility in a few minutes, but at a much lower level, and that level remained constant throughout the experiment.

Compressed disc dissolution studies were carried out by means of the procedure developed by Hamlin et al., *J. Pharm, Sci.,* 51, 432(1962). A 300 mg. sample of powder was compressed against a flat surface at 3000 psi. for 2 minutes into a flat round disc using a tablet die of 7/16 inch diameter. The die holding the compressed disc was stoppered at the open end and placed into a plastic holder. This assembly was then placed into a jar containing 1000 ml. of water equilibrated at 37° C. The stirring rate of a teflon paddle centered in the jar was maintained at 150 revolutions per minute. The solution was pumped continuously through a Millipore filter (0.45 mμ pore size) into a flow cell of a Beckman Acta II spectrophotometer which automatically recorded any absorbance changes at 246 nm.

Table VI compares the intrinsic dissolution rates of various forms of prazosin hydrochloride. The rates were determined from the slopes of the compressed disc dissolution profiles between 4 and 10 minutes.

TABLE VI

Intrinsic Dissolution Rates of Various Forms of
Prazosin Hydrochloride in Water at 37° C.

| Form | Dissolution Rate (μg/liter sec.) |
|---|---|
| α- | 3.25 |
| β- | 3.36 |
| γ- | 2.35 |
| Methanolate | 2.68 |
| Polyhydrate | 2.57 |
| Anhydrate | 2.35 |

From the above characterization studies on the various forms of prazosin hydrochloride it is apparent that the α-form has several important advantages over the other forms. It is the only crystalline, anhydrous form which is non-hygroscopic, and is stable to storage conditions normally encountered, including exposure to sunlight. Also it is readily and reproducibly prepared by methods described herein.

The polyhydrate form of prazosin hydrochloride is also readily prepared by methods described herein. It is stable to normal storage conditions when stored in containers which protect it from sunlight. Examples of such containers are screw-capped amber glass bottles or screw-capped opaque plastic bottles which are well known in the art. A further advantage of the polyhydrate form of prazosin hydrochloride is its low and uniform rate of dissolution, from which it may be concluded that it will provide smoother, more gradual and longer lasting blood levels per unit dose than other forms of this valuable hypotensive agent since it is known in the art that dissolution rate of a drug correlates with its bioavailability. Furthermore, by providing such smooth blood levels of prazosin hydrochloride by administering the polyhydrate form of this valuable hypotensive agent, certain side effects sometimes associated with initial doses of the drug should be minimized.

Since, as noted above, the α-form of prazosin hydrochloride is converted to the polyhydrate by contacting it with an excess of water, the attainment of the same smooth blood levels will be realized with formulations containing the α-form if exposed to an aqueous medium for sufficient time prior to administration of the drug or during its administration but prior to absorption into the blood.

The methanolate form of prazosin hydrochloride suffers the disadvantage of containing the toxic methanol molecule which is likely to have adverse effects if administered to hypotensive subjects.

The β-form of prazosin hydrochloride is hygroscopic and is more difficult to prepare than the preferred α-form and polyhydrate. The γ-form is more hygroscopic then the β-form.

The monohydrate and anhydrate forms of prazosin hydrochloride are less desirable than the preferred α- and polyhydrate forms because they must be prepared from the polyhydrate by extended drying at relatively high temperatures and have been found to revert to polyhydrate upon exposure to moist air.

The preferred α- and polyhydrate forms of prazosin hydrochloride are administered to hypertensive subjects either alone or in combination with pharmaceutically acceptable carriers. The proportion of active ingredient depends upon the chosen route for administration and standard pharmaceutical practice. For example, they may be administered in tablet form with such excipients as lactose, sodium citrate, calcium carbonate and dicalcium phosphate. Various disintegrants such as starch, alginic acid and certain complex silicates together with lubricating agents such as magnesium stearate, sodium lauryl sulfate and talc are often used. For oral administration in capsules, excipients such as lactose and high molecular weight polyethylene glycols may be added. When aqueous suspensions are desired, the active ingredient is combined with emulsifying and/or suspending agents. Diluents such as ethanol, propylene glycol, glycerine and various combinations of diluents are employed. For parenteral administration, solution of the α-form or polyhydrate of prazosin hydrochloride in combination with other solutes such as glucose or saline are used. Such aqueous solutions should be suitably buffered, if necessary, to render them isotonic.

It should be noted that in dosage forms containing a molar excess of water the anhydrous α-form of prazosin hydrochloride becomes hydrated, as shown above.

The dosage required to reduce blood pressure in hypertensive subjects will be determined by the nature and the extent of the hypertension. Generally, small dosages will be administered initially with a gradual increase in dosage until the optimum level is determined. It will generally be found that when the composition is administered orally, larger quantities of the active ingredient will be required to produce the same level of blood pressure reduction as produced by a smaller quantity administered parenterally. In general, from about 0.02 to 10 milligrams of active ingredient per kilogram of body weight administered in single or multiple dosage units effectively reduces blood pressure in hypertensive subjects. Tablets containing 0.5 to 5 milligrams of active ingredient are particularly useful.

The following examples are given by way of illustration and are not to be construed as limiting the invention in any way. Many variations of the invention are possible within the spirit of the invention.

EXAMPLE 1

Prazosin Hydrochloride Methanolate

To 1000 ml. of isoamyl alcohol are added 65.4 g. (0.272 mole) of 2-chloro-4-amino-6,7-dimethoxyquinazoline and 54.0 g. (0.30 mole) of 1-(2-furoyl)piperazine. The mixture was heated at reflux for 3 hours then allowed to stir while cooling to room temperature and stirring continued for an additional 16 hours at ambient temperature. The reaction mixture is cooled to 15° C., filtered, the cake washed with acetone and air dried to obtain 107.2 g. of crude material, M.P. 272°–276°(dec.). This is slurried in 1400 ml. of methanol, heated at reflux temperature for 3 hours, then allowed to cool to room temperature. The solid is isolated by filtration, washed with methanol, then with ether and air dried to afford 110 g. of the title compound as large rod-like crystals, M.P. 276°–278° C. (dec.).

Analysis: Calc'd for $C_{19}H_{21}N_5O_4 \cdot HCL \cdot CH_3OH$ (percent): C, 53.15; H, 5.80; N, 15.50; Cl, 7.85. Found: C, 53.02; H, 5.77; N, 15.47; Cl, 7.79

Thermogravimetric analysis carried out on a DuPont Thermogravimetric Analyzer at a heating rate of 20° C/minute shows a weight loss of 7% occurs at 135° C. This corresponds to a 1:1 methanol: prazosin hydrochloride stoichiometry, in agreement with the above elemental analysis.

EXAMPLE 2

Prazosin Hydrochloride, β-Form

Ten grams of prazosin hydrochloride methanolate, obtained in Example 1 was placed in an oven and held at 110° C., for 24 hours, then cooled to room temperature. The resulting material consisted of monoclinic crystals, M.P. 278°–280° C.

Analysis: Calc'd. for $C_{19}H_{21}N_5O_4$.HCL (percent): C, 54.34; H, 5.28; N, 16.68; Cl, 8.44. Found: C, 54.21; H, 5.26; N, 16.60; Cl, 8.37.

EXAMPLE 3

Prazosin Hydrochloride, γ-Form 2-(1-Piperazinyl)-4-amino-6,7-dimethoxyquinazoline (57.8 g., 0.20 mole) was dissolved in 1000 ml. of chloroform and 30.2 g. (0.20 mole) of 2-furoyl chloride was added slowly at ambient temperature. When the addition was completed the resulting slurry was stirred for 15 minutes after which 1000 ml. of isoamyl alcohol was added. To the resulting mixture was then added sufficient 10% (w/w) aqueous sodium hyroxide solution to effect the solution of the solid material, about 200 ml. was ordinarily required, while maintaining the mixture at room temperature. The aqueous layer was separated and the organic phase was washed with 250 ml. of water. The organic layer was dried over anhydrous $MgSO_4$, filtered and the filtrate cooled to 0° C. Anhydrous hydrogen chloride was passed through the solution at 0°–5° C. until the solution was acidic to moistened test paper (pH about 2–2.5), about 45 minutes was required for the addition. The chloroform was then evaporated at reduced pressure while warming gently to about 45° at 20–30 mm Hg. The vacuum was then released and the solution heated to about 100° C. to remove the last traces of chloroform. The mixture was then allowed to cool to room temperature. The product was recovered by filtration, washed with chloroform and dried in the vacuum oven at 50°–60° C. to afford 73.9 g. of needle-like crystals, M.P. 277°–279° C. (dec.) of the title polymorph.

When a sample of the β-form of prazosin hydrochloride obtained in Example 2 was recrystallized from isoamyl alcohol by heating to about 115° C. then cooling to room temperature, the γ-form was also obtained.

EXAMPLE 4

Prazosin Hydrochloride, α-Form

The procedure of Example 3 was repeated, except that after evaporating the bulk of the chloroform the isoamyl alcohol slurry was heated at reflux (130°–132° C.) for 2 hours. The mixture was then allowed to cool to room temperature, filtered, washed with chloroform and dried in the vacuum oven at 50°–60° C. The resulting rod-like crystals melted at 280°–282° (dec.).

Anal: Calc'd. for $C_{19}H_{21}N_5O_4$.HCl (M.W. 419.87): C, 54,35; H, 5.28; N, 16.68; Cl, 8.44 Found: C, 54.38; H, 5.56; N, 16.71; Cl, 8.41.

When the above procedure is repeated but employing one of the alcohols listed below in place of isoamyl alcohol and heating at the indicated temperature, the results are substantially the same.

| Alcohol | Temperature, ° C. |
|---|---|
| n-Pentanol | 138 |
| n-Hexanol | 156 |
| 2-Methylbutanol | 125 |
| Cyclopentanol | 140 |
| Cyclohexanol | 160 |
| 2-Methyl-3-pentanol | 128 |
| 4-Methyl-1-pentanol | 160 |
| n-Butanol | 130 (in pressure reactor) |
| 2-Methyl-3-hexanol | 142 |
| 5-Methyl-3-hexanol | 147 |
| 2-Methyl-2-hexanol | 140 |
| Cycloheptanol | 160 |

EXAMPLE 5

Conversion of Prazosin Hydrochloride, β-Form to the α-Form

Five grams of the β-form of prazosin .HCl obtained in Example 2 was stirred with 50 ml. of isoamyl alcohol while heating at reflux for 2 hours. The mixture was then allowed to cool to room temperature, washed with chloroform and air dried overnight to afford rod-like crystals. The infrared spectrum (KBr) was identical to that of the α-form of prazosin hydrochloride.

EXAMPLE 6

Conversion of Prazosin Hydrochloride, γ-Form to the α-Form

When the above procedure was repeated with 5 g. of the γ-form of prazosin .HCl obtained in Example 3, the rod shaped crystals of the α-form were also obtained. Again the infrared spectrum (KBr) was superimposible with that of an authentic specimen of Prazosin hydrochloride, α-form.

EXAMPLE 7

Conversion of Prazosin Hydrochloride Methanolate to the α-Form

A 5 g. sample of the methanolate obtained in Example 1 is refluxed for 3 hours in 100 ml. of 2-methylbutanol. The mixture is allowed to cool to room temperature, washed with dichloromethane, and air dried to afford the α-form of prazosin hydrochloride.

EXAMPLE 8

Prazosin Hydrochloride Hydrates and Anhydrate

Prazosin hydrochloride, 180 g., was dissolved in a mixture of 3 liters methanol, 3 liters chloroform and 1200 ml. water. The solution was filtered, then concentrated at atmospheric pressure to 1100 ml. volume. After cooling to room temperature, the precipitated solids were collected by filtration, the cake washed with ethanol, then with hexane, and dried for 3 hours at 60° C. to afford 176 g. of needle-like crystals, M.P. 265°–268° C. (dec.), water by Karl Fisher method: 11.96%. Upon thin-layer chromatography it was found to be identical with an authentic sample of prazosin hydrochloride. Other samples exposed to high humidity contained up to 15% moisture. This compound was designated prazosin hydrochloride polyhydrate.

Upon drying the above polyhydrate in a vacuum desicator at 100° C. for 30 minutes the moisture content was reduced to 7.9% which corresponds to prazosin hydrochloride dihydrate.

When a sample of prazosin hydrochloride polyhydrate was dried in the vaccum desiccator at 100° C. for about 60 minutes, the moisture content was reduced to 4.1% which corresponds to prazosin hydrochloride monohydrate.

Drying in the vacuum desiccator at 100° C. for 12-15 hours afforded the anhydrate form of prazosin hydrochloride, containing about 1% water.

When samples of the anhydrate and monohydrate are stored at room temperature and 75% relative humidity they absorb moisture rapidly to form the dihydrate (8% water) in about 24 hours. The dihydrate continues to absorb water at a slower rate until an equilibrium water content of 13.5% is obtained after 4 days.

EXAMPLE 9

Conversion of the α-Form of Prazosin to the Polyhydrate

To 500 ml. of water, 50 g. of the α-form of prazosin hydrochloride was added and the mixture stirred and heated to 95° C. for 2 hours. After cooling to about 50° C. the slurry was filtered, washed with water and dried in air for 48 hours to obtain 50.5 g. of prazosin hydrochloride polyhydrate containing 12.4% water. The infrared spectrum obtained with a KBr disc was identical to that shown in FIG. II.

EXAMPLE 10

Conversion of Prazosin Hydrochloride Dihydrate to the α-Form

When a sample of prazosin hydrochloride dihydrate was slurried with isoamyl alcohol, then refluxed for 3 hours, cooled and filtered, the rod-like crystals obtained were identified as the α-form by comparison of the infrared spectrum (KBr) with that of an authentic sample of the α-form as shown in FIG. I.

EXAMPLE 11

Tablets

A tablet base is prepared by blending the following ingredients in the proportion by weight indicated:

| | |
|---|---|
| Sucrose, U.S.P. | 80.3 |
| Tapioca starch | 13.2 |
| Magnesium stearate | 6.5 |

Into this base there is blended a sufficient amount of the α-form of 2-[4-(2-furoyl)piperazin-1-yl]-4-amino-6,7-dimethoxyquinazoline hydrochloride to provide tablets containing 0.5, 1, 2 and 5 mg. of active ingredient.

EXAMPLE 12

Capsules

A blend is prepared containing the following ingredients:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added a sufficient amount of the polyhydrate of 2-[4-(2-furoyl)piperazin-1-yl]-4-amino-6,7-dimethoxyquinazoline hydrochloride to provide capsules containing 0.25, 0.5, 1, 2.5 and 5 mg. of active ingredients.

EXAMPLE 13

Injectable Preparation

One thousand grams of the α-form of 2-[4-(2-furoyl)-piperazin-1-yl]-4-amino-6,7-dimethoxyquinazoline hydrochloride is intimately mixed and ground with 2500 grams of sodium ascorbate. The dry mixture is filled into vials, sterilized with ethylene oxide and the vials sterilely stoppered. For intravenous administration sufficient water is added to the vials to form a solution containing 1.0 mg. of active ingredient per milliliter.

EXAMPLE 14

Suspension

A suspension of the polyhydrate of 2-[4-(2-furoyl)piperazin-1-yl]-4-amino-6,7-dimethoxyquinazoline hydrochloride is prepared with the following composition:

| | |
|---|---|
| Effective ingredient | 2.50 g. |
| 70% Aqueous sorbitol | 714.29 g. |
| Glycerine, U.S.P. | 185.35 g. |
| Gum acacia (10% solution) | 100.00 ml. |
| Polyvinylpyrrolidone | 0.50 g. |
| Water, distilled, to make 1 liter | |

To this suspension, various sweetening and flavoring agents may be added by choice. The suspension contains approximately 2.5 mg. of hypotensive agent per milliliter.

What is claimed is:

1. The crystalline α-form of 2-[4-(2-furoyl)piperazin-1-yl]-4-amino-6,7-dimethoxyquinazoline hydrochloride characterized by the infrared spectrum in potassium bromide having the following absorption bands:

| Wavelength, Microns | Wavelength, Microns | Wavelength, Microns |
|---|---|---|
| 2.95 | 7.30 | 10.67 |
| 3.10 | 7.81 | 11.05 |
| 3.25 | 8.08 | 11.30 |
| 3.50 | 8.28 | 11.66 |
| 6.12 | 8.40 | 11.90 |
| 6.26 | 8.70 | 12.60 |
| 6.39 | 9.02 | 13.10 |
| 6.54 | 9.25 | 13.31 |
| 6.75 | 9.60 | 13.87 |
| 6.81 | 9.85 | 13.95 |
| 7.02 | 10.02 | 14.82 |
| 7.22 | | |

2. The process for preparing the crystalline α-form of 2-[4-(2-furoyl)piperazin-1-yl]-4-amino-6,7-dimethoxyquinazoline hydrochloride of claim 1 which comprises precipitation of said α-form after heating 2-[4-(2-furoyl)piperazin-1-yl]-4-amino-6,7-dimethoxyquinazoline hydrochloride, a hydrate or methanolate thereof, in the presence of an alkanol or cycloalkanol solvent having from about 5 to 7 carbon atoms at a temperature in the range of about 125° to 160° C., until formation of said crystalline α-form is substantially complete.

3. The process of claim 2 whrein said alcoholic solvent is isoamyl alcohol.

4. The process of claim 3 wherein said isoamyl alcohol is heated at a temperature of about 132° C.

* * * * *